(12) United States Patent
Coles, Jr. et al.

(10) Patent No.: US 7,877,144 B2
(45) Date of Patent: Jan. 25, 2011

(54) PREDICTING CHRONIC OPTIMAL A-V INTERVALS FOR BIVENTRICULAR PACING VIA OBSERVED INTER-ATRIAL DELAY

(75) Inventors: James A. Coles, Jr., Columbia, MD (US); Michael R. Ujhelyi, Maple Grove, MN (US); Mehdi Razavi, Houston, TX (US); Vadim Levin, Harleysville, PA (US)

(73) Assignee: Medtronic, Inc., Minneapolis, MN (US)

( * ) Notice: Subject to any disclaimer, the term of this patent is extended or adjusted under 35 U.S.C. 154(b) by 802 days.

(21) Appl. No.: 11/460,144

(22) Filed: Jul. 26, 2006

(65) Prior Publication Data

US 2008/0027488 A1 Jan. 31, 2008

(51) Int. Cl.
*A61N 1/365* (2006.01)
*A61N 1/368* (2006.01)
(52) U.S. Cl. .......................................... 607/25
(58) Field of Classification Search .................... 607/9, 607/25
See application file for complete search history.

(56) References Cited

U.S. PATENT DOCUMENTS

| | | | |
|---|---|---|---|
| 5,179,949 A * | 1/1993 | Chirife ........................... | 607/9 |
| 5,331,966 A | 7/1994 | Bennett et al. | |
| 5,720,768 A * | 2/1998 | Verboven-Nelissen ......... | 607/9 |
| 6,871,088 B2 | 3/2005 | Chinchoy | |
| 6,885,889 B2 | 4/2005 | Chinchoy | |
| 7,248,925 B2 * | 7/2007 | Bruhns et al. .................. | 607/25 |
| 2005/0137630 A1 | 6/2005 | Ding et al. | |
| 2005/0137634 A1 * | 6/2005 | Hall et al. ....................... | 607/9 |
| 2005/0149137 A1 | 7/2005 | Chinchoy et al. | |
| 2007/0129762 A1 * | 6/2007 | Worley ........................... | 607/9 |
| 2007/0156194 A1 | 7/2007 | Wang | |

FOREIGN PATENT DOCUMENTS

| | | |
|---|---|---|
| EP | 1 062 987 | 12/2000 |
| EP | 1 260 246 | 11/2002 |
| WO | WO 2007/079343 | 7/2007 |

* cited by examiner

*Primary Examiner*—Carl H. Layno
*Assistant Examiner*—Tammie K Heller
(74) *Attorney, Agent, or Firm*—Stephen W. Bauer; Reed A. Duthler

(57) ABSTRACT

Methods for optimizing the atrio-ventricular (A-V) delay for efficacious delivery of cardiac resynchronization therapy. In CRT devices, the programmed A-V delay starts with detection of electrical activity in the right atrium (RA). Thus, a major component of the A-V delay is the time required for inter-atrial conduction time (IACT) from the RA to the LA. This IACT can be measured during implantation as the time from the atrial lead stimulation artifact to local electrograms in a coronary sinus (CS) catheter. Assuming that the beginning of LA contraction closely corresponds with the beginning of LA electrical activity, the optimal AV delay should be related to the time between the start of RA electrical activity and the start of LA electrical activity plus the duration of LA atrial contraction. Thus 'during atrial pacing' the IACT measured at implantation is correlated with the echocardiographically defined optimal paced AV delay (PAV).

13 Claims, 7 Drawing Sheets

US 7,877,144 B2

PREDICTING CHRONIC OPTIMAL A-V INTERVALS FOR BIVENTRICULAR PACING VIA OBSERVED INTER-ATRIAL DELAY

FIELD OF THE INVENTION

The present invention relates to methods and apparatus for optimally programming for biventricular implantable pulse generators.

BACKGROUND OF THE INVENTION

Congestive heart failure (CHF) is one of the leading causes of cardiovascular morbidity and mortality. With the aging population CHF treatment has become a major public health issue. Recent advances in management of CHF include implantation of biventricular (Bi-V) pacemakers to achieve cardiac resynchronization (CRT). Numerous studies have shown than significant improvements in patients' functional capacity and longevity can be attained when appropriately selected patients receive CRT. Many of the early published trials supporting the benefits of CRT primarily focused on using the patients' intrinsic atrial rate to drive the ventricular pacing rate (VDD mode). However, in clinical practice many CRT recipients are programmed in the dual chamber pacing mode (DDD), which may increase the likelihood of atrial pacing especially given the possibility of better beta-blocker titration with atrial rate support.

By necessity successful delivery of CRT requires biventricular pacing-induced activation of both ventricles prior to intrinsic conduction through the atrioventricular (A-V) node. The programmed A-V delay, or the time between atrial sense/pace and ventricular pace, thus must be sufficiently truncated to preempt intrinsic AV conduction. Programming the A-V delay to optimize left ventricular (LV) filling continues to remain challenging. Many centers perform so-called "A-V optimization" studies using 2-D Doppler echocardiography after implantation. These optimization studies are frequently time consuming and increase the resources required for each implantation. Thus, if the optimal A-V delay could be calculated during initial implantation, such studies would become less necessary.

Applicable prior art relating to CRT includes U.S. Pat. No. 6,885,889 entitled, "Method and Apparatus for Optimizing Cardiac Resynchronization Therapy Based on Left Ventricular Acceleration," and U.S. Pat. No. 6,871,088 entitled, "Method and Apparatus for Optimizing Cardiac Resynchronization Therapy," the entire contents of which are hereby incorporated by reference herein.

SUMMARY

Methods for optimizing the A-V delay in CRT recipients were adopted from those developed for dual-chamber pacemakers; the A-V delay is set such that pacing-induced left ventricular contraction occurs following completion of left atrial (LA) contraction. This maximizes left ventricular filling (preload) which theoretically results in optimal LV contraction via the Frank-Starling mechanism. In CRT devices, the programmed A-V delay starts with detection of electrical activity in the right atrium (RA). Thus, a major component of the A-V delay is the time required for inter-atrial conduction time (IACT) from the RA to the LA. This IACT can be measured during implantation as the time from the atrial lead stimulation artifact to local electrograms in a coronary sinus (CS) catheter. Assuming that the beginning of LA contraction closely corresponds with the beginning of LA electrical activity, the optimal AV delay should be related to the time between the start of RA electrical activity and the start of LA electrical activity plus the duration of LA atrial contraction. Thus, the inventors suggest that during atrial pacing the IACT measured at implantation correlated with the echocardiographically defined optimal paced AV delay (PAV).

DETAILED DESCRIPTION OF THE ILLUSTRATED EMBODIMENTS

In the following detailed description, references are made to illustrative embodiments for optimizing A-V delay interval timing for CRT delivery. Among heart failure patients most likely to benefit from the present invention include, without limitation, those having moderately severe cardiomyopathy (e.g., an ejection fraction less than 35%) with persistent symptoms of Class III or IV heart failure—per the New York Heart Association (NYHA) classification system—despite a stable and optimized medical regimen, dilated LV, and QRS duration greater than about 130 milliseconds (ms).

Figure 1:
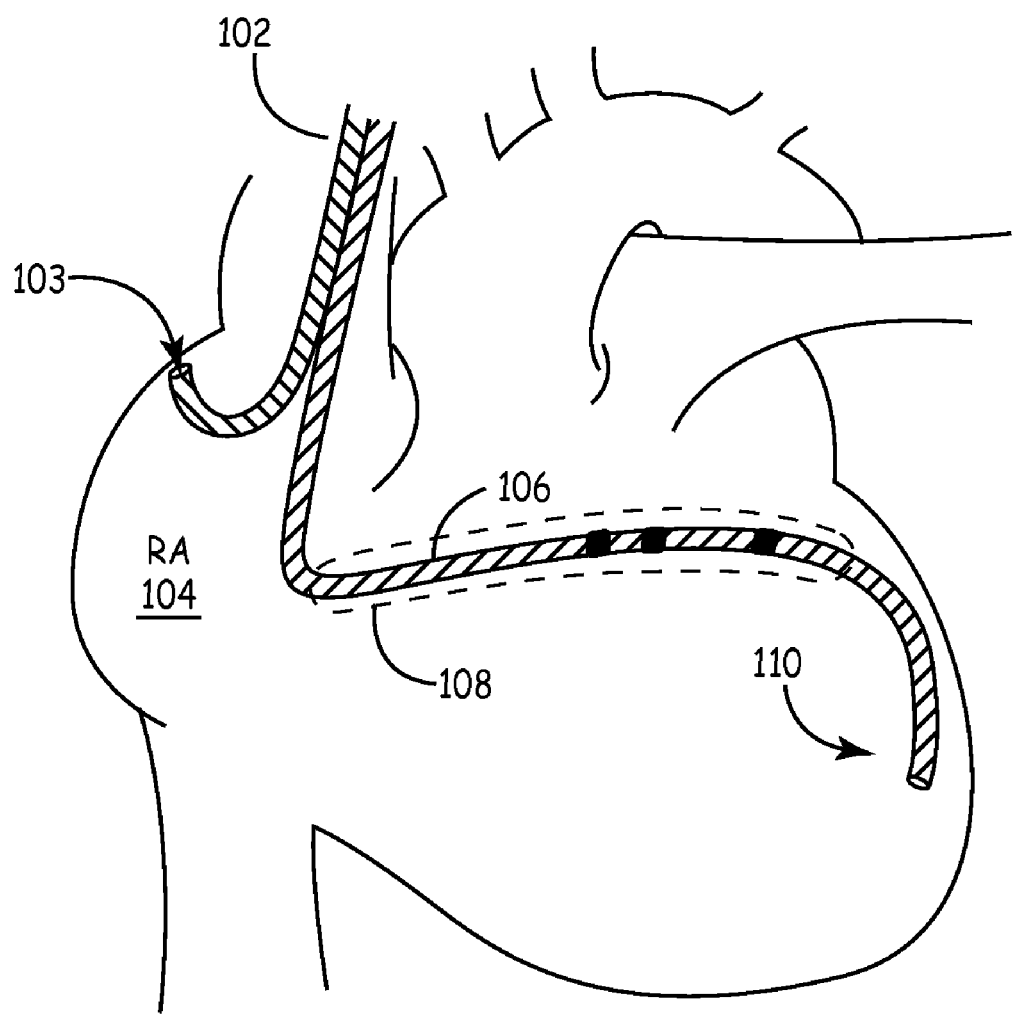
FIG. 1 is a schematic image of a first lead operatively deployed into a right atrial (RA) chamber and a second electrophysiology (EP) catheter deployed through the coronary sinus (CS) and into a portion of a great vein of a subject.

As depicted in FIG. 1, implantation of a medical electrical lead 102 within the RA appendage 104 can be performed before or, preferable, following cannulation of the coronary sinus (CS) 108 with a left-side EP lead 106 deployed into a location within a pulmonary artery 110. A quadripolar EP catheter (e.g., one available from Bard, Viking Quadripolar) or an Amplatz Left-2 (AL-2) catheter with a guidewire can for instance be used to cannulate the CS 108. With the latter technique the EP catheter 106 can be advanced through a guiding sheath (e.g., an Attain® unit available from Medtronic, Inc.) following cannulation of the CS 108. The EP catheter can be advantageously placed so that the proximal recording bipole electrodes s are disposed within the posterolateral CS ("3:00 to 6:00" in the left anterior oblique (LAO) fluoroscopy view (per FIG. 1)). The RA lead 102 couples to a pacing programmer/analyzer (e.g., Medtronic Model 2090) with atrial pacing performed at a rate faster than sinus rhythm (e.g., five beats per minute more rapid). Then IACT is measured. Herein IACT is defined as the interval from the onset of atrial pacing stimulus delivery to the beginning of CS deflection for the bipole in the most posterolateral location (i.e. closest to 4:30 in the LAO view). The process is repeated for RA pacing at 10 and 20 beats per minute faster than sinus rhythm. In the event that a patient has a paced IACT longer than the paced RA-QRS interval they can be excluded from receiving therapy according to the invention. Initially, an EP recording system (Bard LabSystem or GE Prucka) programmed with a recording paper velocity of about 100 mm/second and electrogram signal filtering at 30 to 500 Hz can be used to record IACT. To prove the practicality of this measurement, in later studies the CS catheter was connected to the pacing programmer/analyzer. The CS signals and atrial pacing spikes could be seen on the analyzer and the IACT could be measured. A comparison (in the same procedure) was then made to those measurements made using the EP system. By doing so one can demonstrate that an EP system was not required for IACT measurement (FIG. 2).

Figure 4:
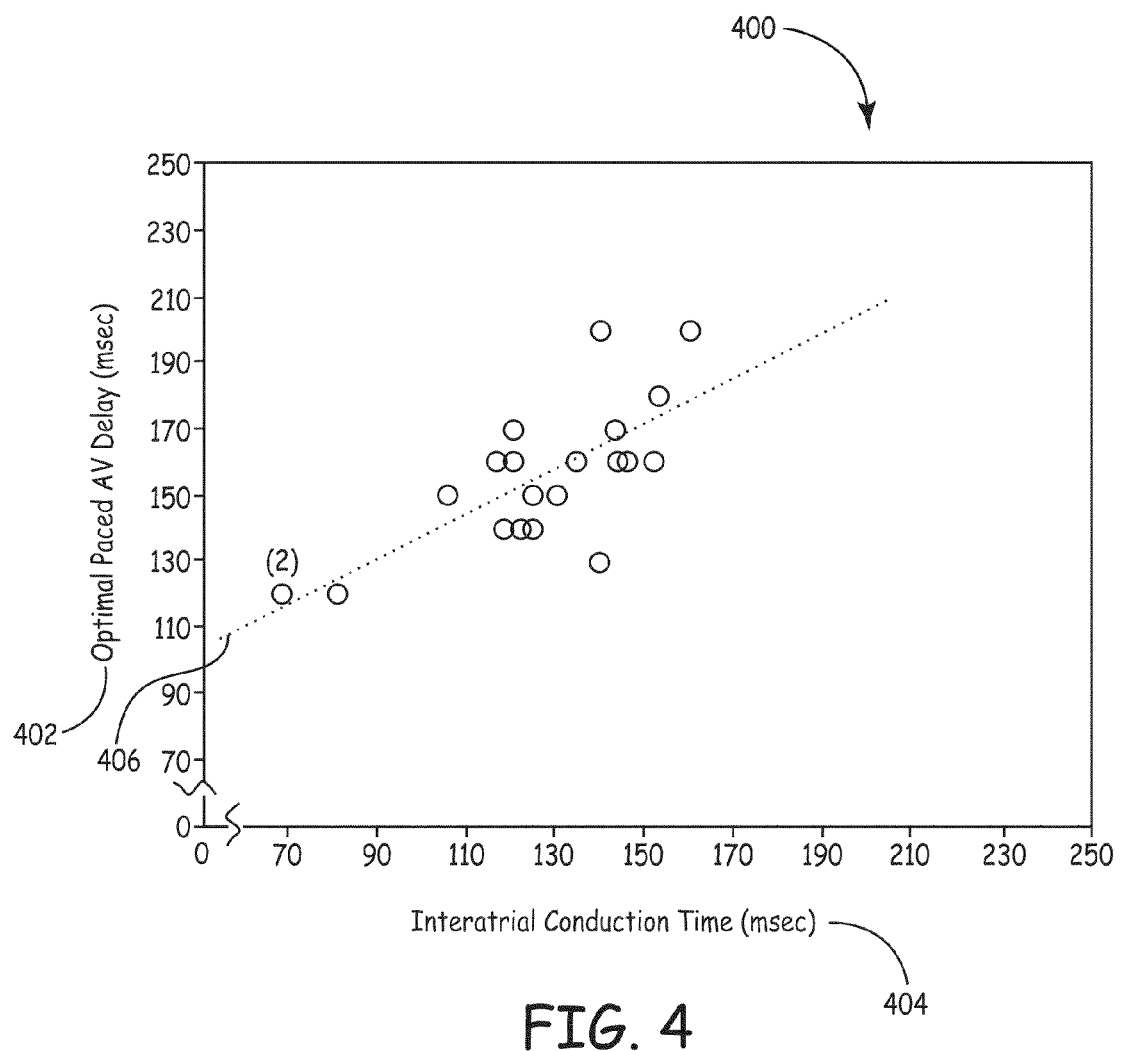
FIG. 4 illustrates the essentially linear relationship between an Optimal Paced AV Delay intervals provided via traditional Doppler ultrasound techniques and inter-atrial conduction time (IACT) according to the present invention.
Figure 5:
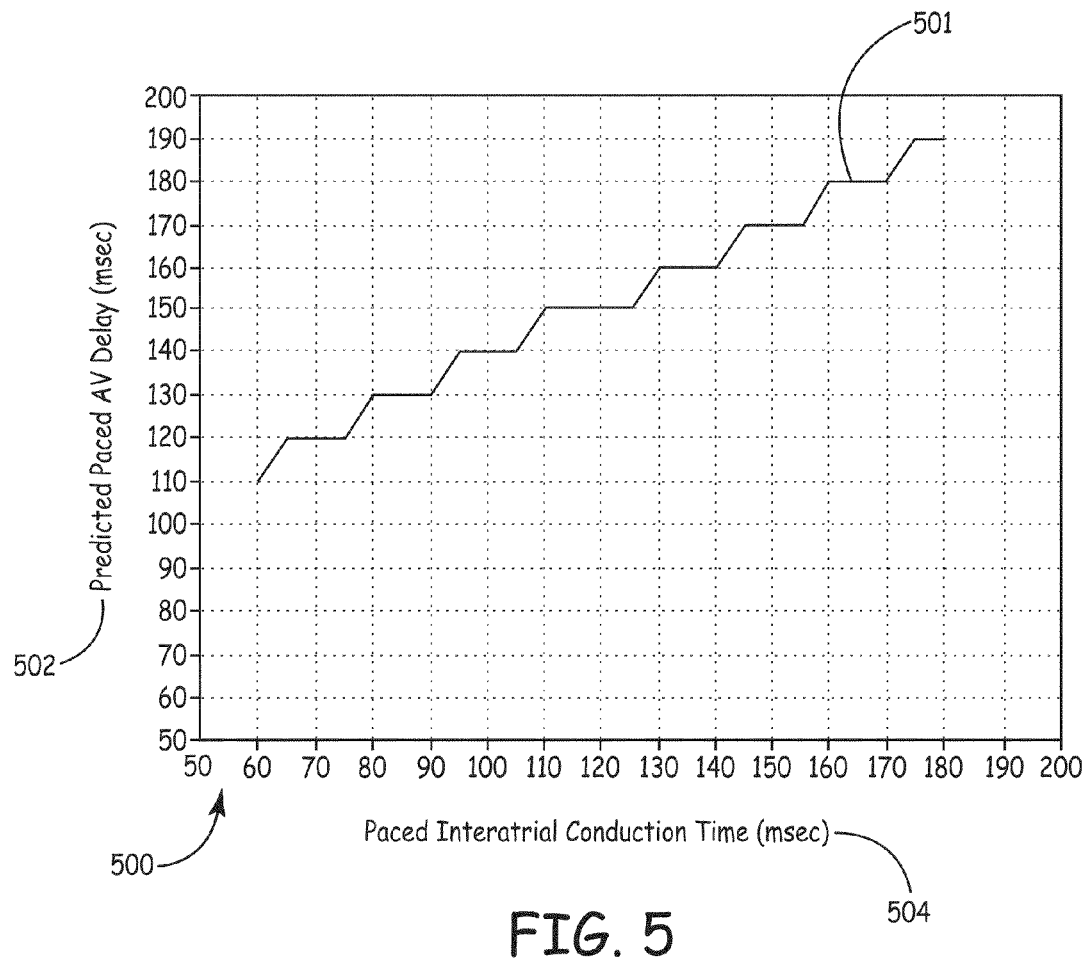
FIG. 5 illustrates how predicted Paced AV Delay intervals relate to IACT according to the present invention.

Subsequent to the implantation and measurement procedures according to the invention (e.g., one day to a week or more) the IACT measurements were compared to traditional Doppler echocardiographic-based AV optimization. The inventors found that the atrial-paced AV delay (PAV) as optimized by the iterative method using transmitral pulsed wave Doppler (FIG. 3) compared extremely favorably with the techniques of the invention. As is known in the art, the traditional iterative method entails: 1) programming a "long" AV delay (but slightly shorter than the patient's intrinsic AV interval); 2) shortening the AV delay by on the order of approximately 20 ms (until the A-wave is truncated by premature mitral valve closure); and 3) prolonging the AV delay (for example by increments of about 10 ms) until the A-wave truncation is eliminated. The iterative method optimizes the AV delay to allow maximal separation of the "E wave" (passive trans-mitral flow) and "A wave" (atrial contraction) without being so short as to produce early closure of the mitral valve. This technique serves to maximize LV filling without causing deleterious diastolic mitral regurgitation (MR). For a group of subjects who assisted in the verification of the present invention, the measured IACT during normal sinus rhythm and atrial pacing were 97±22 (56-140) ms and 127±26 (68-160) ms, respectively. Furthermore, four of the group of patients presented with complete heart block and 17 of the remaining 20 patients had documented first degree AV block. The echo-based PAV determined by the iterative method was 157±24 (120-200) ms. The paced heart rate during implant was 73±16 (40-120) bpm and the device programmed lower rate, which determined the paced heart rate during echocardiography-based PAV optimization was 74±12 (50-90) ms. The heart rate during IACT and PAV measurements were not significantly different. A plot of the individual patient atrial paced IACTs 404 and the optimal PAV intervals 402 is illustrated herewith as FIG. 4. FIG. 4 clearly shows a significant positive correlation between these measurements (r=0.76, p<0.001). However, the relationship between paced IACT and PAV was not 1:1. As expected, the paced IACT 404 (measured to the beginning of LA electrical activation) underestimates the PAV due to the fact that the left atrial (LA) contraction time is not accounted for in the IACT. Hence, the y-intercept 406 of the trend line was greater than zero. The single order equation described the relationship between these measures is thus: PAV=0.69*IACT+69 ms (or PAV=0.69*(IACT+100) ms. Using this equation, a graph of predicted PAV 502 based on paced IACT 504 was developed (as shown in FIG. 5 wherein the PAV is rounded to the nearest decade).

Post-implant echocardiographic atrioventricular optimization of cardiac resynchronization devices can be challenging and time consuming. The results of this study demonstrate that a simple recording at the time of implantation of a cardiac resynchronization device may eliminate the need for AV optimization studies in the post-implant setting. More specifically, measuring the time from the right atrial pacing spike to the start of left atrial electrical activity via a temporary catheter or pacing lead in the distal coronary sinus can be used to predict the paced AV delay with a high degree of accuracy. This is of considerable clinical significance as it may reduce the resources required for optimization of CRT devices.

For CRT to be effective, maintaining a consistently paced ventricular rhythm is necessary. Thus, the AV delay must be programmed to pre-empt intrinsic AV nodal conduction, which could inhibit or fuse with paced ventricular beat and compromise the benefits of CRT. However, the duration of the programmed AV delay must not be too short, as an early paced ventricular contraction will truncate the atrial contribution to LV filling. Nor can the duration be too long for in this case there may be diastolic mitral regurgitation.

The IACT is a critical interval in the interaction between LA emptying and LV filling. This component of the AV delay determines the time it takes for the RA activation to reach the LA. It is at the end of this interval (beginning of CS electrical activity) that LA electrical activity may be approximated to begin. The IACT may therefore estimate the time from RA pacing to the beginning of the transmitral "A" wave. As the IACT prolongs, the AV delay must also be lengthened to accommodate the time needed for LA activation and contraction (A wave). A positive correlation between the IACT and optimal AV delay could thus be expected and was the basis for our hypothesis. Our data confirms a strong, linear correlation between the paced IACT and optimal PAV delay. The AV optimization study was performed without knowledge of any of the intervals obtained during implantation. Optimal PAV delays were defined by the echocardiographer based solely on results of the echo studies.

The IACT can be easily measured and several techniques for measuring IACT have been previously described. In the context of the present invention the only requirements were implantation of the RA lead prior to CS lead implantation and use of a simple non-deflectable quadripolar EP catheter in the distal coronary sinus. Even the LV pacing lead alone could hypothetically be used as it is being guided through the posterolateral CS. Also, this measurement can be performed without need for an EP recording system by connecting the outputs from an EP catheter to the pacing analyzer's input during RA pacing. This aspect of the invention may obviate the need for an EP laboratory or any additional recording equipment.

As noted above, the optimal AV delay is the shortest AV delay which allows complete LV filling while minimizing diastolic mitral regurgitation (MR). The goal of AV optimization is to maximize the diastolic filling time without truncating the A-wave. Thus, during atrial-based Bi-V pacing the optimal PAV delay will allow maximal "E" and "A" wave duration and separation without truncation of the "A" wave by the Doppler signal of diastolic MR. This forms the basis of the iterative echocardiographic optimization method as previously described. Numerous methods of AV optimization have been described yet none have been consistently demonstrated to be superior to others. The inventors are aware of a recent study that compared four echo-based methods of AV optimization to that of invasively measured cardiac contractility (LV dP/dt) and found that the optimal AV delay determined by the maximal velocity-time integral of transmitral inflow best correlated with that determined by the maximal LV dP/dt. In this recent study AV optimization based on maximizing diastolic filling time ("E"+"A" wave duration without "A" wave truncation), which is similar to the iterative method, was also reported to have a strong correlation to optimization using LV dP/dt. Conversely, programming the AV delay to maximize the aortic velocity time integral (cardiac output), was noted to be superior method to AV optimization using transmitral filling. The inventors propose to use the iterative method of AV optimization because it has been previously employed in a large randomized trails of Bi-V pacing and it is commonly described as an AV optimization technique for Bi-V devices.

The present invention provides a simple measurement which can be performed during implantation wherein the PAV may be predicted with a high degree of accuracy. The requirement for such measurements can be found in most non-EP cardiac labs. The technique for obtaining the IACT is flexible and can be incorporated despite various techniques of Bi-V pacemaker implantation. This technique may render unnecessary time consuming and costly echocardiographic studies while maximizing the potential benefit of Bi-V pacing for the patient.

Referring briefly again to the drawings, which are not drawn to scale and in which from time to time like reference numerals are used to represent like structures and/or process steps. FIG. 1 is a fluoroscopy image 100 of a first lead 102 operatively deployed into a right atrial (RA) chamber 104 and a second lead (or electrophysiology (EP) catheter) 106 deployed through the coronary sinus (CS) 108 and into a portion of a great vein 110 of a subject. As is known in the art, the first lead 102 includes an insulated elongated conductor (not shown) disposed within a biocompatible exterior material and at least one electrode 103 couples to the conductor. If a single electrode is used for stimulation and/or sensing cardiac activity of the RA 104 then a unipolar vector is created and typically includes an electrode or a portion of the housing of a pulse generator coupled to the lead 102. However, if at least two electrodes 103 are coupled to the lead 102 then a more localized vector is created between the electrodes.

Figure 2A:
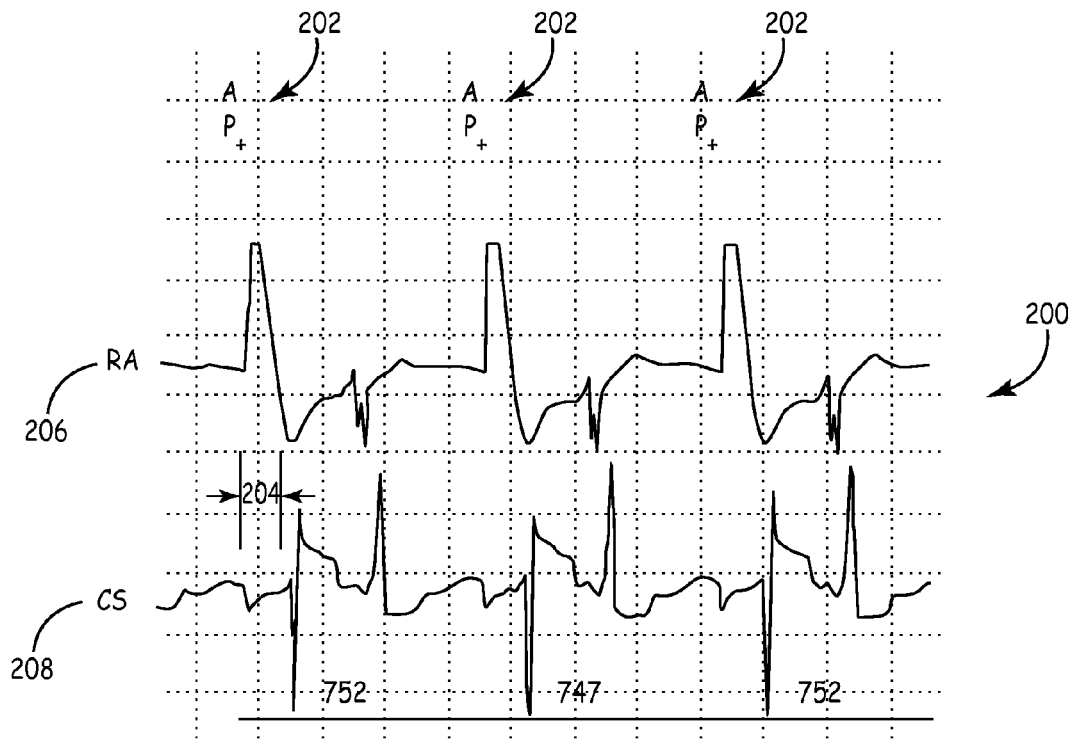
FIGS. 2A and 2B are temporal traces of cardiac activity as provided from output signals from the first lead and the second lead of FIG. 1.

FIG. 2A depicts temporal traces 200 of cardiac activity as provided from output signals from the first lead 102 and the second lead 106 of FIG. 1 following delivery of atrial pacing stimulus (AP) 202. The IACT 204 is the period of time between the initial deflection as sensed in the RA (trace 206) and the initial deflection caused by the depolarization wave front as detected by lead 106 in a portion of the great vein ("CS" in FIG. 2A) 208.

Figure 2B:
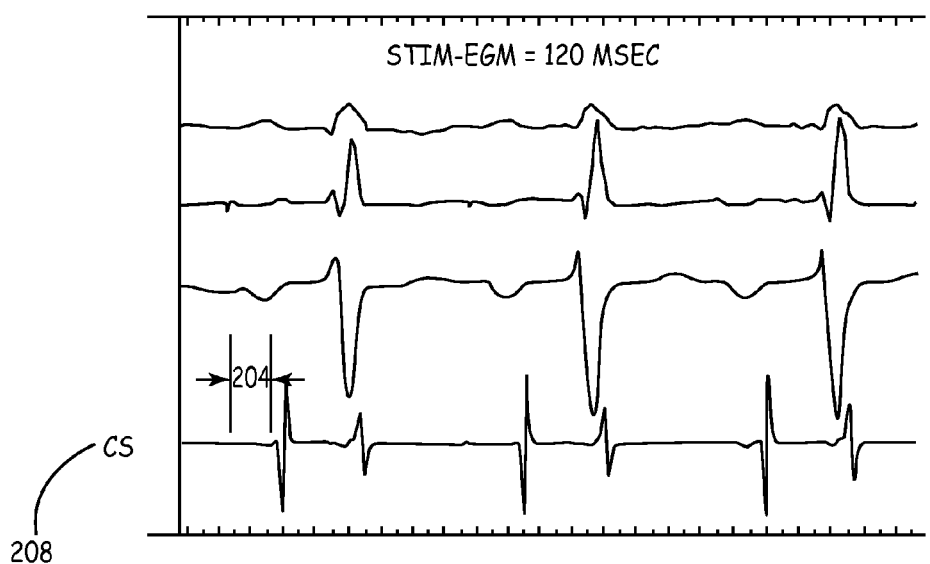

FIG. 2B, like FIG. 2A, depicts the IACT 204 as the interval between atrial stimulation delivered to the RA and the resulting depolarization wavefront arriving at an electrode deployed in the CS 208.

Figures 3A, 3B, 3C:
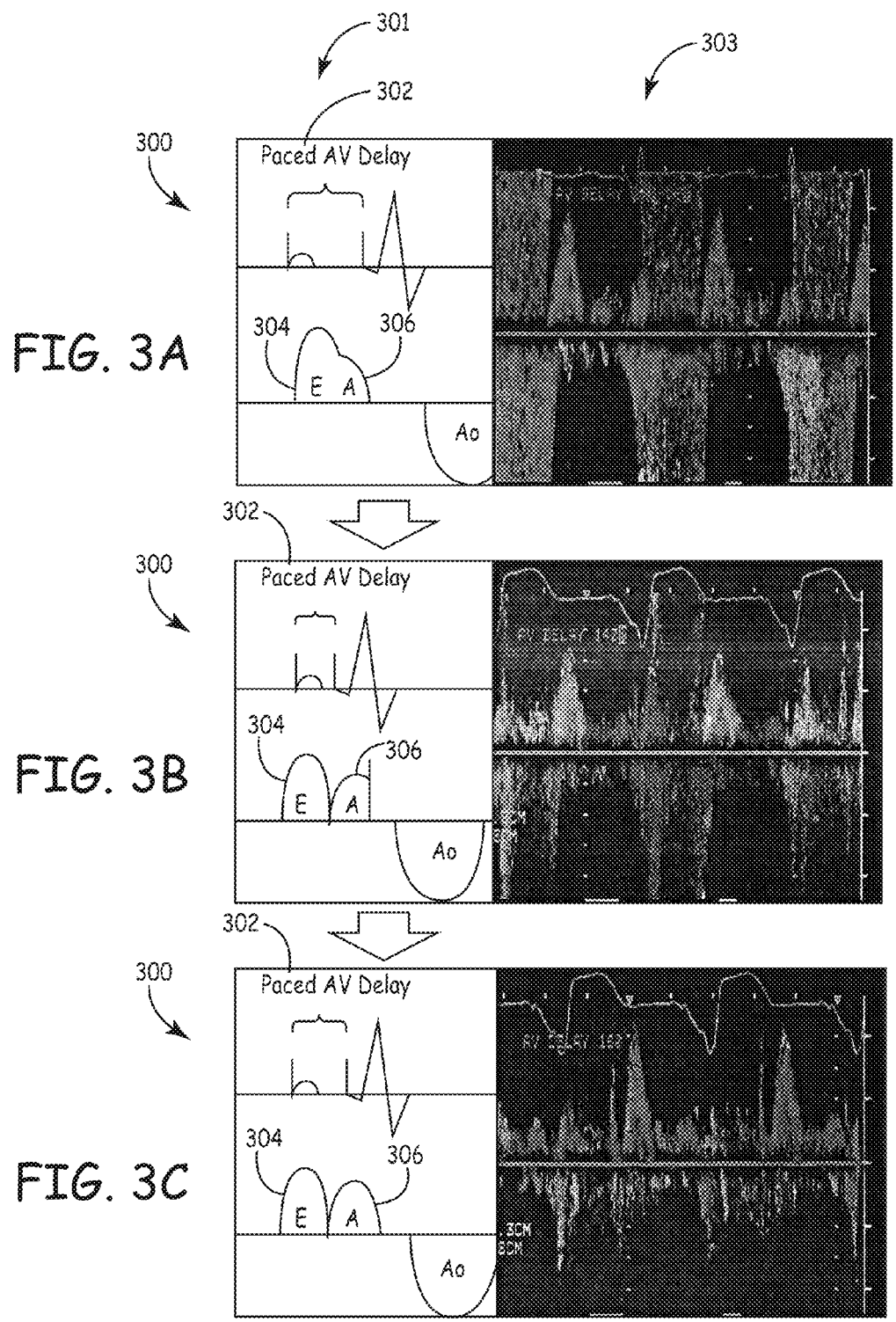
FIGS. 3A to 3C are each a combination of a textural description, a symbolic representation, and a Doppler ultrasound image illustrating how changing AV intervals alters the amount and timing of blood entering and ejecting from the cardiac chambers.

FIGS. 3A to 3C are each a combination 300 a symbolic representation 301 and a Doppler ultrasound image 303 illustrating how changing AV delay 302 intervals alters the amount and timing of blood entering and ejecting from the cardiac chambers. Such that in FIG. 3A, a long AV delay interval 302 can be seen to shorten diastole causing fusion of the E and A waves 304,306, respectively of trans-mitral flow and/or loss of complete ventricular capture.

As depicted in FIG. 3B, shortening the PAV 302 causes A wave truncation wherein ventricular systole starts prior to completion of atrial filling. That is, the A wave 306 is truncated by early closure of the mitral valve or reversal of flow (MR).

Now referring to FIG. 3C one can appreciate that an optimal AV delay interval 302 (which oftentimes has a magnitude about 10-20 ms longer than the AV delay that resulted in A wave truncation) results in separation of the E wave 304 and the A wave 306 with minimal, if any, truncation of the A wave 306.

FIG. 4 illustrates the essentially linear relationship 400 between Optimal Paced AV (PAV) delay intervals 403 provided via traditional Doppler ultrasound techniques and interatrial conduction time (IACT) 404 according to the present invention.

FIG. 5 illustrates how predicted PAV delay intervals 502 relate to IACT 504 according to the present invention. The solid line 501 can be utilized as the basis for programming in an acute setting such as an operating room during implant. However, once a patient has stabilized the data can be collected and stored in a memory structure, such as a look up table (LUT) with a correlation to heart rate and/or activity sensor signal output for dynamic AV delay adjustment based on a patient's status. In order to meaningfully correlate IACT to heart rate and/or activity a patient could be subject to a treadmill or hall walk exercise or the like so that heart rate excursions and/or activity sensor signals could be collected in the context of varying IACT values, for example.

Figure 6:
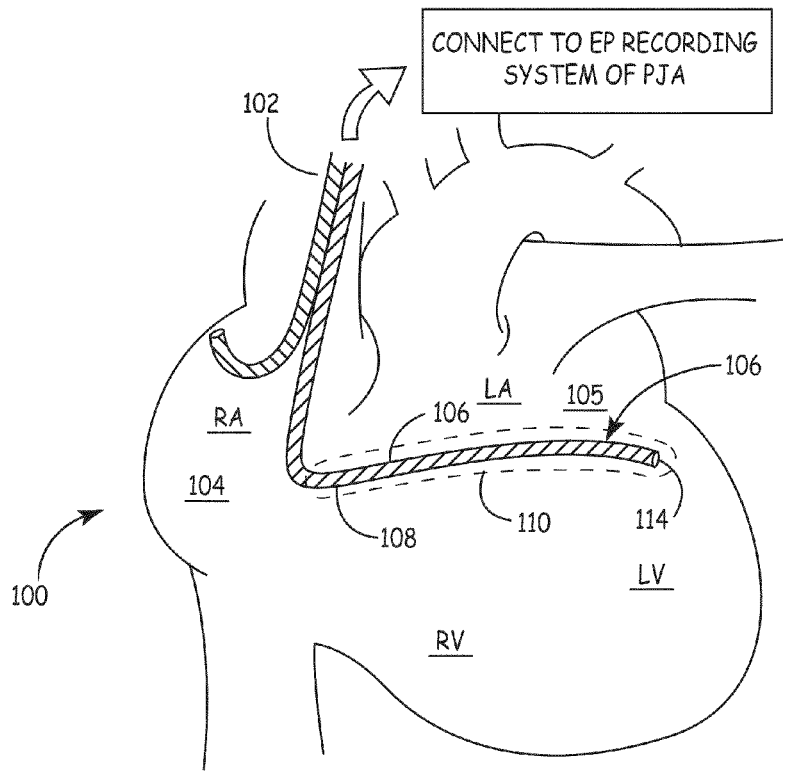
FIG. 6 illustrates in schematic form the nominal deployment of the first lead and the second lead (or catheter) of FIG. 1 during initial, or pre-implant, placement of electrodes for a bi-ventricular (Bi-V) pacing engine according to the invention.

FIG. 6 illustrates in schematic form 100 the nominal deployment of the first lead 102 into the RA 104 and the second lead (or catheter) 106 of FIG. 1 during initial, or pre-implant, placement of electrodes for a bi-ventricular (Bi-V) pacing engine according to the invention.

Figure 7:
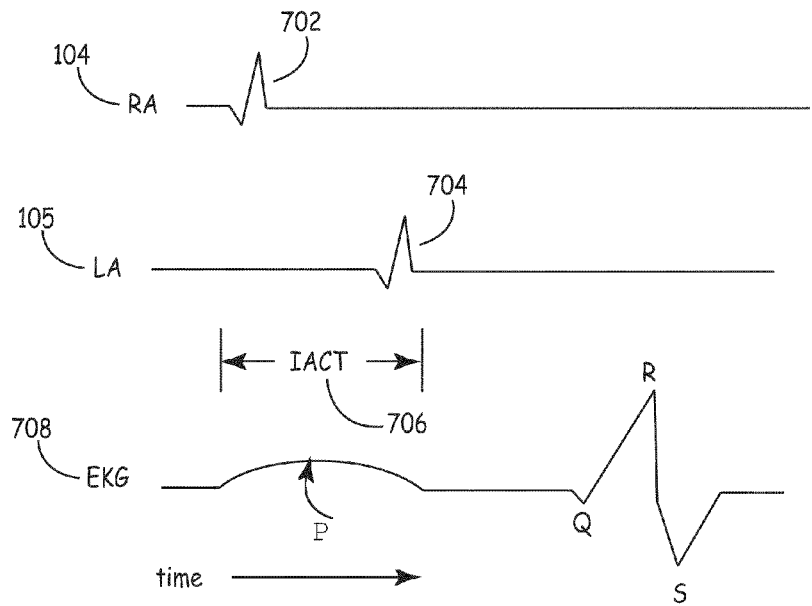
FIG. 7 is a temporal representation of the IACT for a given cardiac cycle of a patient.

FIG. 7 is a temporal representation of the IACT for a given cardiac cycle of a patient wherein the RA 104 deflection due to receipt of pacing stimulus (or intrinsic depolarization) is recorded at 702 and the subsequent wavefront is recorded in the LA 105 at 704. Thus, the IACT 706 is the time between recorded events 702 and 704. At 708 a temporal ECG tracing is depicted wherein the relatively prolonged P wave (representing a composite of event 704 and 706) is shown preceding the typical QRS waveform of a ventricular depolarization.

Figure 8:
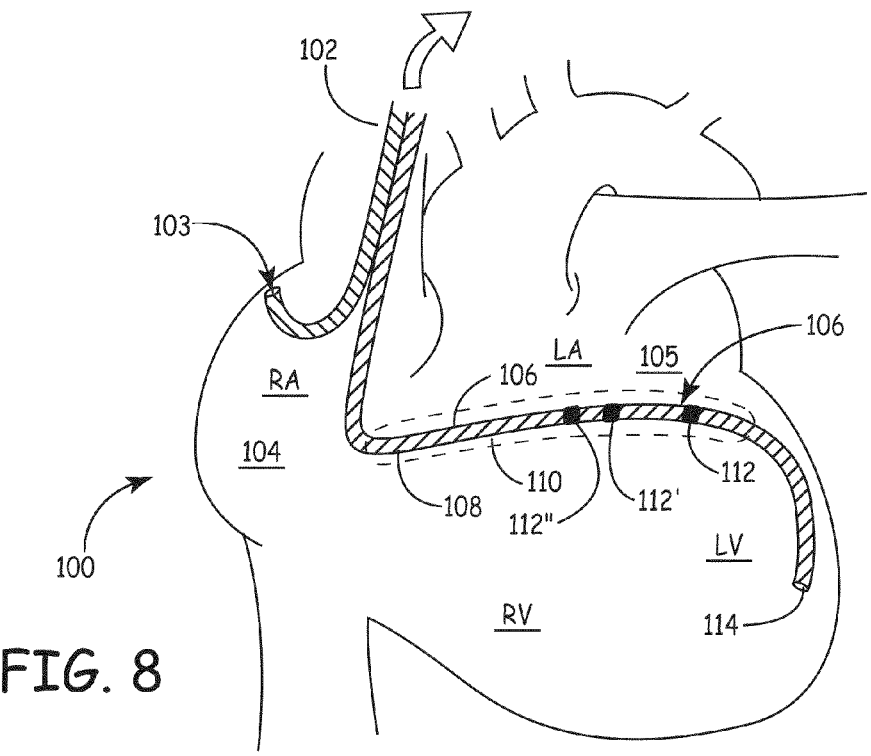
FIG. 8 illustrates in schematic form the nominal deployment of the first lead and the second lead (or catheter) of FIG. 1 during a follow-up (post-implant) visit showing the relative placement of electrodes for a Bi-V pacing engine according to the invention.

FIG. 8 illustrates in schematic form the nominal deployment of the first lead 102 and the second lead (or catheter) 106 of FIG. 1 during a follow-up (post-implant) visit showing the relative placement of electrodes for a Bi-V pacing engine according to the invention. In the depicted embodiment, the second lead 106 is deployed through the CS 108 and into a portion of the great vein 110 as depicted and described previously. However, in this embodiment a plurality of electrodes 112,112',112" are operatively coupled to the second lead 106. The electrodes 112,112',112" can be operated to provide a plurality of sensing vectors used to measure the IACT. In addition, the second lead 106 is shown having a fixation apparatus 114 coupled to its distal tip, although apparatus 114 could be combination electrode and fixation apparatus as is known in the art.

Figure 9:
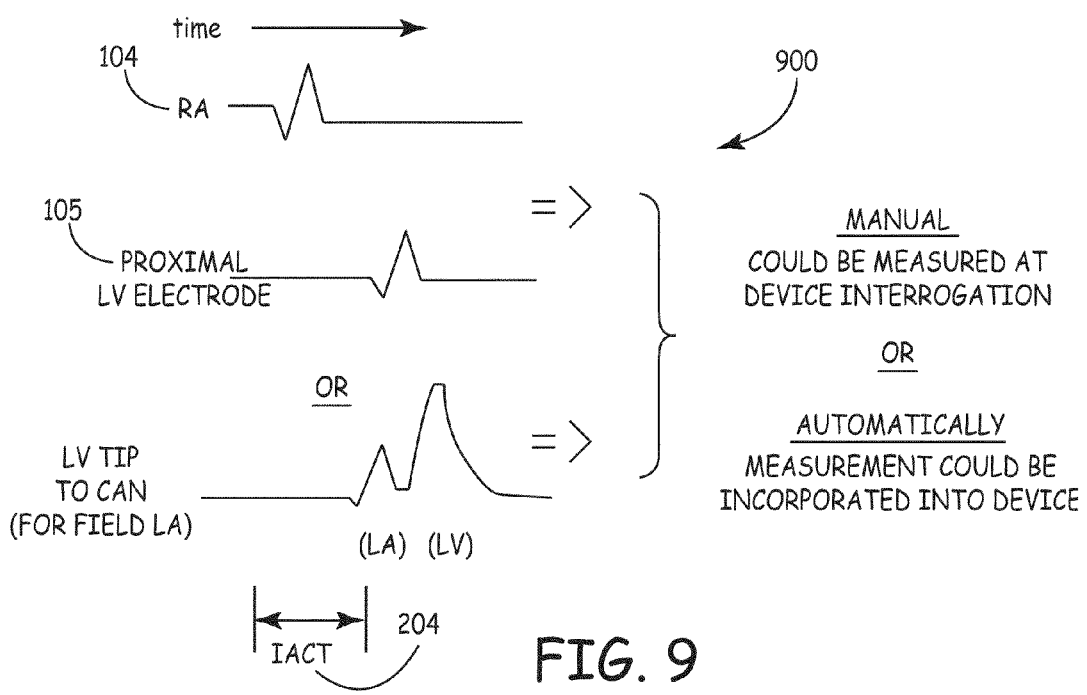
FIG. 9 is a temporal representation of the IACT for a given cardiac cycle of a patient showing two different sensing vectors used to determine the IACT of a subject.

FIG. 9 is a temporal representation of the IACT 204 for a given cardiac cycle of a patient showing two different sensing vectors (from the electrode 103 deployed in the RA 104 to one of the electrodes 112,112',112" used to determine the IACT of a subject. Also depicted is a sensed waveform from the optional electrode 114 to an electrode disposed on a portion of a housing for the pulse generator (not depicted) which is known as "far-field sensing"

The present invention provides enhanced and expedient means of programming an optimal A-V delay interval for biventricular implantable pulse generators adapted to delivery therapy to heart failure patients and others suffering from cardiac insufficiency. While certain embodiments have been described and/or depicted herein in the context of AV interval optimization in an acute, post- or intra-implantation procedure the invention can be practiced chronically in vivo. In such an embodiment, a look up table (LUT) or equivalent can be used to store optimized AV intervals for a range of heart rates and/or activity sensor signals.

Also, in the event that a system according to the invention performs an IACT duration test and the IACT duration differs by a given value from a prior value (used to set an optimized AV interval) then an alarm or notification can be issued that an AV interval optimization procedure should be performed.

Regarding the types of electrodes used in a chronically-implanted system according to the invention a multi-polar electrode (e.g., quadra-, hexa-, deca-polar or the like) can be deployed into a portion of the great vein. In this case, the various vectors can be used to determine the best vectors for measuring IACT and in the event of electrode dislodgement or malfunction, a different electrode vector can be implemented. In addition, a pericardial (or epicardial) electrode or array of electrodes can be used in lieu of or in addition to the foregoing. Also, far-field sensing can be performed using a subcutaneous device, such as an extra-cardiac ICD deployed near the cardiac notch or in an intercostal space.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method for programming an atrio-ventricular (A-V) delay interval for a bi-ventricular implantable pulse generator, comprising:
   determining an inter-atrial conduction time (IACT) between an evoked depolarization of a right atrium (RA) and a conducted depolarization of a left atrium (LA);
   calculating an atrio-ventricular (AV) delay interval based upon the IACT, wherein the calculating step comprises adding about 100 milliseconds to the IACT value to produce a resulting value and reducing the resulting value by about 31 percent; and
   subsequently delivering for at least one cardiac cycle a bi-ventricular pacing therapy to a right ventricle (RV) and to a left ventricle (LV) upon expiration of the calculated AV delay interval.

2. A method according to claim 1, wherein the step of determining the IACT comprises stimulating the RA and sensing conducted depolarization of the LA via a bi-polar electrode pair deployed upon an acutely implantable catheter.

3. A method according to claim 2, wherein the catheter comprises one of an electrophysiology (EP) catheter and a chronically implantable medical electrical lead having at least four discretely addressable electrodes operatively coupled to a distal portion thereof.

4. A method according to claim 3, wherein the EP catheter is adapted for deployment via a guiding sheath portion.

5. A method according to claim 3, wherein the EP catheter is adapted for deployment via the coronary sinus (CS) and into a portion of a great vein.

6. A method according to claim 5, wherein the portion of the great vein comprises a posterolateral portion of the great vein.

7. An apparatus for programming an atrio-ventricular (A-V) delay interval for a bi-ventricular implantable pulse generator, comprising:
   means for determining an inter-atrial conduction time (IACT) between an evoked depolarization of a right atrium (RA) and a conducted depolarization of a left atrium (LA);
   means for calculating an atrio-ventricular (AV) delay interval based upon the IACT, wherein the means for calculating further includes adding about 100 milliseconds to the IACT value to produce a resulting value and reducing the resulting value by about 31 percent; and
   means for subsequently delivering for at least one cardiac cycle a bi-ventricular pacing therapy to a right ventricle (RV) and to a left ventricle (LV) upon expiration of the calculated AV delay interval.

8. An apparatus according to claim 7, wherein the means for determining the IACT further includes means for stimulating the RA and means for sensing conducted depolarization of the LA via a bi-polar electrode pair deployed upon an acutely implantable catheter.

9. An apparatus according to claim 8, wherein the catheter comprises an electrophysiology (EP) catheter having at least four discretely addressable electrodes operatively coupled to a distal portion thereof.

10. An apparatus according to claim 9, wherein the EP catheter is adapted for deployment via a guiding sheath portion.

11. An apparatus according to claim 9, wherein the EP catheter is adapted for deployment via the coronary sinus (CS) and into a portion of a great vein.

12. An apparatus according to claim 11, wherein the portion of the great vein comprises a posterolateral portion of the great vein.

13. An apparatus according to claim 7, further comprising an external pulse generator coupled to a medical electrical lead, and wherein the generator coupled to the lead is adapted to initiate the evoked depolarization of the RA.

* * * * *